(12) United States Patent
Chapman et al.

(10) Patent No.: US 7,147,638 B2
(45) Date of Patent: Dec. 12, 2006

(54) ELECTROSURGICAL INSTRUMENT WHICH REDUCES THERMAL DAMAGE TO ADJACENT TISSUE

(75) Inventors: Troy J. Chapman, Englewood, CO (US); Chelsea Shields, Boulder, CO (US); David A. Schechter, Longmont, CO (US)

(73) Assignee: Sherwood Services AG, Schaffhausen (CH)

( * ) Notice: Subject to any disclaimer, the term of this patent is extended or adjusted under 35 U.S.C. 154(b) by 145 days.

(21) Appl. No.: 10/834,764

(22) Filed: Apr. 29, 2004

(65) Prior Publication Data

US 2005/0004570 A1 Jan. 6, 2005

Related U.S. Application Data

(60) Provisional application No. 60/467,027, filed on May 1, 2003.

(51) Int. Cl.
*A61B 18/18* (2006.01)
(52) U.S. Cl. ............................ 606/51; 606/49; 606/50; 606/52
(58) Field of Classification Search ............ 606/49–52, 606/205
See application file for complete search history.

(56) References Cited

U.S. PATENT DOCUMENTS

| | | | |
|---|---|---|---|
| 371,664 A | 10/1887 | Brannan et al. | |
| 702,472 A | 6/1902 | Pignolet | |
| 728,883 A | 5/1903 | Downes | |
| 1,586,645 A | 6/1926 | Bierman | |
| 2,002,594 A | 5/1935 | Wappler et al. | |
| 2,011,169 A | 8/1935 | Wappler | |
| 2,031,682 A | 2/1936 | Wappler et al. | |
| 2,176,479 A | 10/1939 | Willis | |
| 2,305,156 A | 12/1942 | Grubel | |
| 2,632,661 A | 3/1953 | Cristofv | |
| 2,668,538 A | 2/1954 | Baker | |
| 2,796,065 A | 6/1957 | Kapp | |
| 3,459,187 A | 8/1969 | Pallotta | |
| 3,643,663 A | 2/1972 | Sutter | |
| 3,651,811 A | 3/1972 | Hildebrandt et al. | |
| 3,862,630 A | 1/1975 | Balamuth | |
| 3,866,610 A | 2/1975 | Kletschka | |
| 3,911,766 A | 10/1975 | Fridolph et al. | |
| 3,920,021 A | 11/1975 | Hiltebrandt | |
| 3,921,641 A | 11/1975 | Hulka | |
| 3,938,527 A | 2/1976 | Rioux et al. | |

(Continued)

FOREIGN PATENT DOCUMENTS

CA 2104423 2/1994

(Continued)

OTHER PUBLICATIONS

PCT/US01/11340, International Search Report.

(Continued)

*Primary Examiner*—Michael Peffley
*Assistant Examiner*—Alex Toy

(57) ABSTRACT

An electrode sealing assembly for use in combination with an electrosurgical instrument includes first and second jaw members which are movable from a first, spaced-apart position to a second position to grasp tissue. Each of the jaw members includes an insulative housing, a thermally conductive, electrically non-conductive material and a sealing plate. The insulative housing has a series of electromechanical interfaces which mate with a corresponding series of electromechanical interfaces which extend from the sealing plate such that the sealing plates are a capable of conducting bipolar energy through tissue held between the jaw members. The thermally conductive, electrically non-conductive material is configured to encapsulate and secure the sealing plate to the insulative housing.

14 Claims, 7 Drawing Sheets

U.S. PATENT DOCUMENTS

| | | |
|---|---|---|
| 3,952,749 A | 4/1976 | Fridolph et al. |
| 4,005,714 A | 2/1977 | Hiltebrandt |
| 4,041,952 A | 8/1977 | Morrison, Jr. et al. |
| 4,074,718 A | 2/1978 | Morrison, Jr. |
| 4,088,134 A | 5/1978 | Mazzariello |
| 4,128,099 A | 12/1978 | Bauer |
| 4,165,746 A | 8/1979 | Burgin |
| 4,300,564 A | 11/1981 | Furihata |
| 4,370,980 A | 2/1983 | Lottick |
| 4,416,276 A | 11/1983 | Newton et al. |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,763,669 A | 8/1988 | Jaeger |
| 4,827,929 A | 5/1989 | Hodge |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Kamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| 5,330,471 A | 7/1994 | Eggers |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,425,739 A | 6/1995 | Jessen |
| 5,429,616 A | 7/1995 | Schaffer |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A * | 8/1995 | Stern et al. .................... 606/51 |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,312 A * | 3/1996 | Klicek ........................ 606/34 |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,542,945 A | 8/1996 | Fritzsch |
| 5,558,672 A | 9/1996 | Edwards et al. |
| 5,562,699 A | 10/1996 | Heimberger et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,582,611 A | 12/1996 | Tsuruta et al. |
| 5,585,896 A | 12/1996 | Yamazaki et al. |
| 5,590,570 A | 1/1997 | LeMaire, III et al. |
| 5,601,601 A | 2/1997 | Tal et al. |
| 5,603,711 A | 2/1997 | Parins et al. |
| 5,603,723 A | 2/1997 | Aranyi et al. |
| 5,611,798 A | 3/1997 | Eggers |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,658,281 A | 8/1997 | Heard |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,681,282 A | 10/1997 | Eggers et al. |
| 5,688,270 A * | 11/1997 | Yates et al. .................... 606/51 |

| | | | | | |
|---|---|---|---|---|---|
| 5,693,051 A | 12/1997 | Schulze et al. | D424,694 S | 5/2000 | Tetzlaff et al. |
| 5,695,522 A | 12/1997 | LeMaire, III et al. | D425,201 S | 5/2000 | Tetzlaff et al. |
| 5,700,261 A | 12/1997 | Brinkerhoff | 6,059,782 A | 5/2000 | Novak et al. |
| 5,702,390 A | 12/1997 | Austin et al. | RE36,795 E | 7/2000 | Rydell |
| 5,707,369 A | 1/1998 | Vaitekunas et al. | 6,083,223 A | 7/2000 | Baker |
| 5,709,680 A * | 1/1998 | Yates et al. .................... 606/50 | 6,086,586 A * | 7/2000 | Hooven ....................... 606/50 |
| 5,716,366 A * | 2/1998 | Yates .......................... 606/139 | 6,090,107 A | 7/2000 | Borgmeier et al. |
| 5,720,744 A | 2/1998 | Eggleston et al. | 6,096,031 A | 8/2000 | Mitchell et al. |
| 5,727,428 A | 3/1998 | LeMaire, III et al. | 6,096,037 A | 8/2000 | Mulier et al. |
| 5,735,848 A | 4/1998 | Yates et al. | 6,099,550 A | 8/2000 | Yoon |
| 5,743,906 A | 4/1998 | Parins et al. | 6,102,909 A | 8/2000 | Chen et al. |
| 5,755,717 A | 5/1998 | Yates et al. | 6,110,171 A | 8/2000 | Rydell |
| 5,766,130 A | 6/1998 | Selmonosky | 6,113,596 A | 9/2000 | Hooven et al. |
| 5,766,166 A | 6/1998 | Hooven | 6,113,598 A | 9/2000 | Baker |
| 5,766,170 A | 6/1998 | Eggers | 6,117,158 A | 9/2000 | Measamer et al. |
| 5,769,849 A | 6/1998 | Eggers | 6,123,701 A | 9/2000 | Nezhat |
| 5,772,655 A | 6/1998 | Bauer et al. | H1904 H | 10/2000 | Yates et al. |
| 5,772,670 A | 6/1998 | Brosa | 6,126,658 A | 10/2000 | Baker |
| 5,776,128 A | 7/1998 | Eggers | 6,152,923 A | 11/2000 | Ryan |
| 5,776,130 A | 7/1998 | Buysse et al. | 6,174,309 B1 | 1/2001 | Wrublewski et al. |
| 5,779,701 A | 7/1998 | McBrayer et al. | 6,179,834 B1 | 1/2001 | Buysse et al. |
| 5,792,137 A | 8/1998 | Carr et al. | 6,179,837 B1 | 1/2001 | Hooven |
| 5,792,177 A | 8/1998 | Kaseda | 6,183,467 B1 | 2/2001 | Shapeton et al. |
| 5,797,938 A | 8/1998 | Paraschac et al. | 6,187,003 B1 | 2/2001 | Buysse et al. |
| 5,797,958 A | 8/1998 | Yoon | 6,190,386 B1 | 2/2001 | Rydell |
| 5,800,449 A | 9/1998 | Wales | 6,193,718 B1 | 2/2001 | Kortenbach et al. |
| 5,807,393 A | 9/1998 | Williamson, IV et al. | 6,206,876 B1 | 3/2001 | Levine et al. |
| 5,810,808 A | 9/1998 | Eggers | 6,206,877 B1 | 3/2001 | Kese et al. |
| 5,810,811 A * | 9/1998 | Yates et al. .................... 606/50 | 6,217,602 B1 | 4/2001 | Redmon |
| 5,810,877 A | 9/1998 | Roth et al. | 6,224,593 B1 | 5/2001 | Ryan et al. |
| 5,814,043 A | 9/1998 | Shapeton | 6,228,080 B1 | 5/2001 | Gines |
| 5,817,093 A | 10/1998 | Williamson, IV et al. | 6,228,083 B1 | 5/2001 | Lands et al. |
| 5,820,630 A | 10/1998 | Lind | 6,267,761 B1 | 7/2001 | Ryan |
| 5,827,271 A | 10/1998 | Buysse et al. | 6,270,497 B1 | 8/2001 | Sekino et al. |
| 5,827,279 A | 10/1998 | Hughett et al. | 6,270,508 B1 | 8/2001 | Klieman et al. |
| 5,827,281 A | 10/1998 | Levin | 6,273,887 B1 * | 8/2001 | Yamauchi et al. ............ 606/48 |
| 5,833,690 A * | 11/1998 | Yates et al. .................... 606/52 | 6,277,117 B1 * | 8/2001 | Tetzlaff et al. ................ 606/48 |
| 5,843,080 A | 12/1998 | Fleenor et al. | 6,280,458 B1 | 8/2001 | Boche et al. |
| 5,849,022 A | 12/1998 | Sakashita et al. | 6,283,961 B1 | 9/2001 | Underwood et al. |
| 5,853,412 A | 12/1998 | Mayenberger | D449,886 S | 10/2001 | Tetzlaff et al. |
| 5,860,976 A | 1/1999 | Billings et al. | 6,322,561 B1 | 11/2001 | Eggers et al. |
| 5,876,401 A | 3/1999 | Schulze et al. | 6,334,860 B1 | 1/2002 | Dorn |
| 5,891,141 A | 4/1999 | Rydell | 6,334,861 B1 | 1/2002 | Chandler et al. |
| 5,891,142 A | 4/1999 | Eggers et al. | 6,350,264 B1 | 2/2002 | Hooven |
| 5,893,863 A | 4/1999 | Yoon | 6,352,536 B1 | 3/2002 | Buysse et al. |
| 5,893,875 A | 4/1999 | O'Connor et al. | D457,958 S | 5/2002 | Dycus et al. |
| 5,893,877 A | 4/1999 | Gampp, Jr. et al. | D457,959 S | 5/2002 | Tetzlaff et al. |
| 5,902,301 A | 5/1999 | Olig | 6,387,094 B1 | 5/2002 | Eitenmuller |
| 5,906,630 A | 5/1999 | Anderhub et al. | 6,398,779 B1 | 6/2002 | Buysse et al. |
| 5,908,420 A | 6/1999 | Parins et al. | 6,402,747 B1 | 6/2002 | Lindemann et al. |
| 5,911,719 A | 6/1999 | Eggers | 6,409,728 B1 | 6/2002 | Ehr et al. |
| 5,913,874 A | 6/1999 | Berns et al. | H2037 H | 7/2002 | Yates et al. |
| 5,921,984 A | 7/1999 | Sutcu et al. | 6,419,675 B1 | 7/2002 | Gallo, Sr. |
| 5,925,043 A | 7/1999 | Kumar et al. | 6,425,896 B1 | 7/2002 | Baltschun et al. |
| 5,935,126 A | 8/1999 | Riza | 6,443,952 B1 | 9/2002 | Mulier et al. |
| 5,944,718 A | 8/1999 | Austin et al. | 6,443,970 B1 | 9/2002 | Schulze et al. |
| 5,951,549 A | 9/1999 | Richardson et al. | 6,451,018 B1 | 9/2002 | Lands et al. |
| 5,954,720 A | 9/1999 | Wilson et al. | 6,458,128 B1 | 10/2002 | Schulze |
| 5,957,923 A | 9/1999 | Hahnen et al. | 6,458,130 B1 | 10/2002 | Frazier et al. |
| 5,961,514 A | 10/1999 | Long et al. | 6,464,704 B1 | 10/2002 | Schmaltz et al. |
| 5,976,132 A | 11/1999 | Morris | 6,484,701 B1 | 11/2002 | Liu |
| 5,984,939 A | 11/1999 | Yoon | 6,503,248 B1 | 1/2003 | Levine |
| 5,989,277 A | 11/1999 | LeMaire, III et al. | 6,506,189 B1 | 1/2003 | Rittman, III et al. |
| 6,004,335 A | 12/1999 | Vaitekunas et al. | 6,508,815 B1 | 1/2003 | Strul et al. |
| 6,010,516 A | 1/2000 | Hulka et al. | 6,511,480 B1 * | 1/2003 | Tetzlaff et al. ................ 606/51 |
| 6,024,741 A | 2/2000 | Williamson, IV et al. | 6,514,251 B1 | 2/2003 | Ni et al. |
| 6,024,744 A | 2/2000 | Kese et al. | 6,544,264 B1 | 4/2003 | Levine et al. |
| 6,033,399 A | 3/2000 | Gines | 6,569,162 B1 | 5/2003 | He |
| 6,039,733 A | 3/2000 | Buysse et al. | 6,585,735 B1 | 7/2003 | Frazier et al. |
| 6,041,679 A | 3/2000 | Slater et al. | 6,620,161 B1 | 9/2003 | Schulze et al. |
| 6,050,996 A | 4/2000 | Schmaltz et al. | 6,652,521 B1 | 11/2003 | Schulze |
| 6,053,914 A | 4/2000 | Eggers et al. | 6,656,177 B1 | 12/2003 | Truckai et al. |
| 6,053,933 A | 4/2000 | Balazs et al. | 6,669,696 B1 | 12/2003 | Bacher et al. |

| | | | | | | |
|---|---|---|---|---|---|---|
| 6,676,660 B1 * | 1/2004 | Wampler et al. ............... 606/51 | EP | 0364216 A1 | 4/1990 |
| 6,682,528 B1 | 1/2004 | Frazier et al. | EP | 0518230 A1 | 12/1992 |
| 6,685,724 B1 | 2/2004 | Haluck | EP | 0 541 930 A1 | 5/1993 |
| 6,733,498 B1 | 5/2004 | Paton et al. | EP | 0572131 | 12/1993 |
| 6,743,229 B1 | 6/2004 | Buysse et al. | EP | 0584787 A1 | 3/1994 |
| 6,773,409 B1 * | 8/2004 | Truckai et al. ................. 601/2 | EP | 0623316 A1 | 11/1994 |
| 6,773,434 B1 | 8/2004 | Ciarrocca | EP | 0624348 A2 | 11/1994 |
| 6,776,780 B1 | 8/2004 | Mulier et al. | EP | 0650701 A1 | 5/1995 |
| D496,997 S | 10/2004 | Dycus et al. | EP | 0694290 A3 | 3/1996 |
| 6,802,843 B1 | 10/2004 | Truckai et al. | EP | 0717966 A1 | 6/1996 |
| D499,181 S | 11/2004 | Dycus et al. | EP | 0754437 A3 | 3/1997 |
| 6,818,000 B1 | 11/2004 | Muller et al. | EP | 0853922 A1 | 7/1998 |
| 6,926,716 B1 * | 8/2005 | Baker et al. .................. 606/51 | EP | 0875209 A1 | 11/1998 |
| 6,929,644 B1 | 8/2005 | Truckai et al. | EP | 0878169 A1 | 11/1998 |
| 6,932,816 B1 * | 8/2005 | Phan ........................... 606/49 | EP | 0887046 A3 | 1/1999 |
| 6,942,662 B1 | 9/2005 | Goble et al. | EP | 0923907 A1 | 6/1999 |
| 6,964,662 B1 | 11/2005 | Kidooka | EP | 0986990 A1 | 3/2000 |
| 2002/0013583 A1 | 1/2002 | Camran et al. | EP | 1034747 A1 | 9/2000 |
| 2002/0099372 A1 | 7/2002 | Schulze et al. | EP | 1034748 A1 | 9/2000 |
| 2002/0107517 A1 | 8/2002 | Witt et al. | EP | 1025807 A3 | 10/2000 |
| 2002/0111624 A1 | 8/2002 | Witt et al. | EP | 1034746 A3 | 10/2000 |
| 2002/0188294 A1 | 12/2002 | Couture et al. | EP | 1050278 A1 | 11/2000 |
| 2003/0018331 A1 | 1/2003 | Dycus et al. | EP | 1053719 A1 | 11/2000 |
| 2003/0069571 A1 | 4/2003 | Treat et al. | EP | 1053720 A1 | 11/2000 |
| 2003/0078578 A1 | 4/2003 | Truckai Csaba et al. | EP | 1055399 A1 | 11/2000 |
| 2003/0139741 A1 | 7/2003 | Goble et al. | EP | 1055400 A1 | 11/2000 |
| 2003/0139742 A1 | 7/2003 | Wampler et al. | EP | 1080694 A1 | 3/2001 |
| 2003/0158549 A1 | 8/2003 | Swanson | EP | 1082944QA1 | 3/2001 |
| 2003/0199869 A1 | 10/2003 | Johnson et al. | EP | 1159926 A2 | 12/2001 |
| 2003/0216732 A1 | 11/2003 | Truckai et al. | EP | 1330991 A1 | 7/2003 |
| 2003/0220637 A1 | 11/2003 | Truckai et al. | EP | 14881772 A2 | 6/2004 |
| 2003/0236325 A1 | 12/2003 | Bonora | EP | 1532932 A1 | 5/2005 |
| 2004/0030330 A1 | 2/2004 | Brassell et al. | GB | 2214430 A | 6/1989 |
| 2004/0030332 A1 | 2/2004 | Knowlton et al. | JP | 501068 | 8/1984 |
| 2004/0049185 A1 | 3/2004 | Latterell et al. | JP | 502328 | 3/1992 |
| 2004/0116979 A1 | 6/2004 | Truckai et al. | JP | 5-40112 | 2/1993 |
| 2004/0147925 A1 | 7/2004 | Buysse et al. | JP | 06343644 A2 | 12/1994 |
| 2004/0176762 A1 * | 9/2004 | Lawes et al. ................. 606/51 | JP | 06343844 A2 | 12/1994 |
| 2004/0225288 A1 | 11/2004 | Buysse et al. | JP | 07265328 A2 | 10/1995 |
| 2004/0230189 A1 | 11/2004 | Keppel | JP | 08056955 A2 | 3/1996 |
| 2004/0236325 A1 * | 11/2004 | Tetzlaff et al. ................. 606/51 | JP | 08252263 A2 | 10/1996 |
| 2004/0243125 A1 | 12/2004 | Dycus et al. | JP | 09010223 A2 | 1/1997 |
| 2004/0249371 A1 | 12/2004 | Dycus et al. | JP | 11244298 A2 | 9/1999 |
| 2004/0249374 A1 | 12/2004 | Tetzlaff et al. | JP | 200350732 A2 | 12/2000 |
| 2004/0250419 A1 | 12/2004 | Sremcich et al. | JP | 2000342599 A2 | 12/2000 |
| 2004/0254573 A1 | 12/2004 | Dycus et al. | JP | 2000350732 A2 | 12/2000 |
| 2005/0004564 A1 | 1/2005 | Wham et al. | JP | 2001008944 A2 | 1/2001 |
| 2005/0004568 A1 | 1/2005 | Lawes et al. | JP | 2001029356 A2 | 2/2001 |
| 2005/0004570 A1 | 1/2005 | Chapman et al. | JP | 2001128990 A2 | 5/2001 |
| 2005/0021025 A1 | 1/2005 | Buysse et al. | SU | 401367 | 10/1973 |
| 2005/0021026 A1 | 1/2005 | Baily | SU | 401367 | 11/1974 |
| 2005/0021027 A1 | 1/2005 | Shields et al. | WO | WO 92/06642 | 4/1992 |
| 2005/0033278 A1 | 2/2005 | McClurken et al. | WO | WO 94/08524 A | 4/1994 |
| 2005/0101951 A1 | 5/2005 | Wham et al. | WO | WO 95/02369 | 1/1995 |
| 2005/0101952 A1 | 5/2005 | Lands et al. | WO | WO 95/07662 | 3/1995 |
| 2005/0107764 A1 | 5/2005 | Moses et al. | WO | WO 96/13218 | 9/1996 |
| 2005/0107785 A1 | 5/2005 | Dycus et al. | WO | WO 97/00646 | 1/1997 |
| 2005/0113818 A1 | 5/2005 | Sartor et al. | WO | WO 97/00647 | 1/1997 |
| 2005/0113819 A1 | 5/2005 | Wham et al. | WO | WO 97/10764 | 3/1997 |
| 2005/0113826 A1 | 5/2005 | Johnson et al. | WO | WO 97/24073 | 7/1997 |
| 2005/0113827 A1 | 5/2005 | Dumbauld et al. | WO | WO 97/24993 | 7/1997 |
| 2005/0113828 A1 | 5/2005 | Shields et al. | WO | WO 96/022058 | 7/1998 |
| 2005/0119655 A1 | 6/2005 | Moses et al. | WO | WO 98/27880 | 7/1998 |
| 2005/0149151 A1 | 7/2005 | Orszulak et al. | WO | WO 89/03409 | 1/1999 |
| 2006/0079891 A1 | 4/2006 | Arts et al. | WO | WO 99/03407 | 1/1999 |
| | | | WO | WO 99/03408 | 1/1999 |
| FOREIGN PATENT DOCUMENTS | | | WO | WO 99/12488 A | 3/1999 |
| | | | WO | WO 99/40857 | 8/1999 |
| DE | 2415263 | 10/1975 | WO | WO 99/040881 | 8/1999 |
| DE | 871232 B | 3/1988 | WO | WO 99/51158 | 10/1999 |
| DE | 29616210 | 1/1997 | WO | WO 99/66850 A | 12/1999 |
| DE | 19608716 | 4/1997 | WO | WO 99/068850 | 12/1999 |
| DE | 19751108 | 5/1999 | WO | WO 00/24330 | 5/2000 |

| | | |
|---|---|---|
| WO | WO 00/24331 | 5/2000 |
| WO | WO 00/41638 | 7/2000 |
| WO | WO 00/53112 | 9/2000 |
| WO | WO 01/17448 A | 3/2001 |
| WO | WO 01/54604 | 8/2001 |
| WO | WO 02/07627 | 1/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080796 A1 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/101311 | 12/2003 |
| WO | WO 04/032777 | 4/2004 |
| WO | WO 2004/052221 A1 | 6/2004 |
| WO | WO 04/073490 | 9/2004 |
| WO | WO 04/082495 | 9/2004 |
| WO | WO 2004/082495 | 9/2004 |
| WO | WO 2004/098383 A1 | 11/2004 |
| WO | WO 04/103156 | 12/2004 |

OTHER PUBLICATIONS

PCT/US01/11420, International Search Report.
PCT/US02/01890, International Search Report.
PCT/US02/11100, International Search Report.
PCT/US04/03436, International Search Report.
PCT/US04/13273, International Search Report.
PCT/US04/15311, International Search Report.
EP 98944778, International Search Report.
EP 98958575, International Search Report.
EP 04027479, International Search Report.
EP 04027705, International Search Report.
EP 04027314, International Search Report.
Sigel et al. "The Mechanism of Blood Vessel Closure by High Frequency Electrocoagulation" Surgery Gynecology & Obstetrics, Oct. 1965 pp. 823-831.
Bergdahi et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington Univsersity School of Medicine, St. Louis MO, Presented at AHPBA, Feb. 2001.
Johnson et al. "Evaluation of the LigaSure Vessel Sealing System in Hamorrholdectormy" American College of Surgeons (ACS) Clinicla Congress Poster (2000).
Sayfan et al. "Sutureless Closed hamorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasts During Pelvic Surgery" Int'l. Federation of Gynecology and Obstetrics FIGO World Congress 2000, Washington, D.C.
Levy et al. "Use of a New Energy-based Vessel Ligation Device during Vaginal Hysterectomy" Int'l Federation of Gynecology and Obstetrics (FIGO) World Congress.

Crawford et al. "Use of the LigaSure Vessel Sealing System in Urologic Cancer Suger" Grand Rounds in Urology 1999 vol. 1 Issue 4 pp. 10-17.
Rothenberg et al. "Use of the LigaSure Vessel Sealing system in Minimally Invasive Surgery in Children" Int'l Pediatric Endosurgery Group (IPEG) 2000.
Palazzo et al. "Randomized clinical trial of Ligaure versus open haamorrholdectomy" British Journal of Surgery 2002, 89, 154-157
"Innovations in Electrosurgery" Sales/Product Literature.
LigaSure Vessel Sealing System, the Seal of Confidence in General, Gynecologic, Urologic, and Laparaoscopic Surgery Sales/Product Literature.
Carbonell et al. "comparison of theGyrus PlasmaKinetic Sealer and the Valleytab LigaSure Device in the Hemostasis of Small, Medium, and Large-Sized Arteries" Carolinas Laparoscopic and Advanced Surgery Program, Carolinas Medical Center, Charlotte, NC.
"Reducing Needlestick Injuries in the Operating Room" Sales/Product Literature.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, □Apr. 2001 pp. 236-237.
W. Scott Helton, "LigaSure Vessel Sealing System: Revolutionary Hemostasis Product for General Surgery" Sales/Product Literature.
Michael Choti, "Abdominoperineal Resection with the LigaSure Vessel Sealing System and LigaSure Atlas 20 om Open Instrument" Innovations that Work, □Jun. 2003.
Craig Johnson, "Use of the LigaSure Vessel Sealing System in Bloodless Hamorrhoidectomy" Innovations That Work, □Mar. 2000.
Muller et al., "Extended Left Hemicolectomy Using the LigaSure Vessel Sealing System" Innovations That Work,□Sep. 1999.
Herman et al., "Laparoscopic Intestinal Resection With the LigaSure Vessel Sealing System: A Case Report" Innovations That Work,□Feb. 2002.
Carus et al., "Initial Experience With The LigaSure Vessel Sealing System in Abdominal Surgery" Innovations That Work,□Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing For Hemostasis During Gynecologic Surgery" Sales/Product Literature.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" current Surgical Techniques in Urology, vol. 14, Issue 3.
E. David Crawford "Use of a Novel Vessel Sealing Technology in Management of the Dorsal Veinous Complex" Sales/Product Literature.
Jarrett et al., "Use of the LigaSure Vessel Sealing System for Peri-Hilar Vessels in Laparoscopic Nephretomy" Sales/Product Literature.
E. David Crawford "Evaluation of a New Vessel Sealing Device in Urologic Cancer Surgery" Sales/Product Literature.
Joseph Ortenberg "LigaSure System used in Laparoscopic 1st and 2nd Stage Orchiopexy" Innovations That Work, Nov. 2002.
Koyle et al. "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature.

Johnson et al. "Evaluation of a Bipolar electrothermal Vessel Sealing Device in Hemorrhoidectomy" Sales/Product Literature.
Int'l Search Report PCT/US01/11218.
Int'l Search Report PCT/US99/24869.
Int'l Search Report PCT/US98/18640.
Int'l Search Report PCT/US98/23950.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan., 2004.
Olsson et al. "Radical Cystectomy in Females" Current Surgical Techniques in Urology, vol. 14, Issue 3, 2001.
Dulemba et al. "Use of a Bipolar Electrothermal Vessel Sealer in Laparoscopically Assisted Vaginal Hysterectomy" Sales Product Literature; Jan., 2004.
Johnson et al. "Evaluation of a Bipolar electrothermal Vessel Sealing Device in Hemorrhoidectomy" Sales Product Literature; Jan., 2004.
International Search Report PCT/US01/11224 dated Nov. 13, 2001.
International Search Report EP 98958575.7 dated Sep. 20, 2002.
International Search Report EP 04013772 dated Apr. 1, 2005.
International Search Report EP 05013895 dated Oct. 14, 2005.
International Search Report EP 05017281 dated Nov. 16, 2005.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report —extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 05016399 dated Jan. 5, 2006.
Int'l Search Report EP 06005185.1 dated Apr. 18, 2006.
US 6,663,629, 12/2003, Buysse et al. (withdrawn)

* cited by examiner

ELECTROSURGICAL INSTRUMENT WHICH REDUCES THERMAL DAMAGE TO ADJACENT TISSUE

CROSS REFERENCE TO RELATED APPLICATION

The present application claims the benefit of priority to U.S. Provisional Application Ser. No. 60/467,027 filed on May 1, 2003 by Chapman et al., the entire contents of which being incorporated by reference herein.

BACKGROUND

The present disclosure relates to electrosurgical instruments used for open and endoscopic surgical procedures for sealing or fusing tissue. More particularly, the present disclosure relates to a bipolar forceps for sealing vessels, vascular tissues and soft tissues having an electrode sealing assembly which is designed to limit and/or reduce thermal spread to adjacent tissue structures.

TECHNICAL FIELD

Electrosurgical forceps utilize both mechanical clamping action and electrical energy to effect hemostasis by heating the tissue and blood vessels to coagulate and/or cauterize vessels or tissue. However, certain surgical procedures may require sealing blood vessels or vascular tissue rather than just simply effecting hemostasis. "Vessel sealing" or "Tissue Fusion" is defined as the process of liquefying the collagen, elastin and ground substances in the tissue so that it reforms into a fused mass with significantly-reduced demarcation between the opposing tissue structures. In contrast, the term "cauterization" is defined as the use of heat to destroy tissue (also called "diathermy" or "electrodiathermy") and the term "coagulation" is defined as a process of desiccating tissue wherein the tissue cells are ruptured and dried. Coagulation of small vessels is usually sufficient to permanently close them. Larger vessels or tissue need to be "sealed" to assure permanent closure.

Numerous electrosurgical instruments have been proposed in the past for various open and endoscopic surgical procedures. However, most of these instruments cauterize or coagulate tissue and are normally not designed to provide uniformly reproducible pressure on the blood vessel or tissue which, if used for sealing purposes, would result in an ineffective or non-uniform seal. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cauterizing, and cutting vessels or tissue.

Many of these instruments include blade members or shearing members which simply cut tissue in a mechanical and/or electromechanical manner and are relatively ineffective for vessel sealing purposes. Other instruments generally rely on clamping pressure alone to procure proper sealing thickness and are often not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

Commonly-owned U.S. Application Ser. Nos. PCT Application Ser. No. PCT/US01/11340 filed on Apr. 6, 2001 by Dycus, et al. entitled "VESSEL SEALER AND DIVIDER", U.S. application Ser. No. 10/116,824 filed on Apr. 5, 2002 by Tetzlaff et al. entitled "VESSEL SEALING INSTRUMENT" and PCT Application Ser. No. PCT/US01/11420 filed on Apr. 6, 2001 by Tetzlaff et al. entitled "VESSEL SEALING INSTRUMENT" teach that to effectively seal tissue or vessels, especially large vessels, two predominant mechanical parameters must be accurately controlled: 1) the pressure applied to the vessel; and 2) the gap distance between the conductive tissue contacting surfaces (electrodes). As can be appreciated, both of these parameters are affected by the thickness of the vessel or tissue being sealed. Accurate application of pressure is important for several reasons: to reduce the tissue impedance to a low enough value that allows enough electrosurgical energy through the tissue; to overcome the forces of expansion during tissue heating; and to contribute to the end tissue thickness which is an indication of a good seal.

It has been found that using electrosurgical instruments to seal tissue may result in some degree of so-called "thermal spread" across adjacent tissue structures. "Thermal spread" refers generally to the heat transfer traveling along the periphery of the electrically conductive surfaces. This can also be termed "collateral damage" to adjacent tissue. As can be appreciated, reducing the thermal spread during an electrical procedure reduces the likelihood of unintentional or undesirable collateral damage to surrounding tissue structures which are adjacent to an intended treatment site. Reducing the collateral damage to surrounding tissue or maintaining the viability of surrounding tissue after the sealing process is known to promote tissue healing and decrease overall healing time by stimulating/improving healing response.

Instruments which include dielectric coatings disposed on the outer surfaces are known and are used to prevent tissue "blanching" at points normal to the sealing site. In other words, these coatings are primarily designed to reduce accidental burning of tissue as a result of incidental contact with the outer surfaces of the end effectors. So far as is known these coating are not designed or intended to reduce collateral tissue damage or thermal spread to adjacent tissue (tissue lying along the tissue plane).

Commonly-owned U.S. patent Ser. No. 10/474,168 entitled "ELECTROSURGICAL INSTRUMENT WHICH REDUCES COLLATERAL DAMAGE TO ADJACENT TISSUE" filed on Oct. 3, 2003 by Buysse et al. relates to an instrument which is configured to control or regulate the electrical field around the electrically conductive sealing surfaces to reduce stray current concentrations which can result in thermal spread to adjacent tissue structures.

Thus, a need exists to develop an electrosurgical instrument which includes an electrode sealing assembly which can seal vessels and tissue consistently and effectively and reduce the undesirable effects of thermal spread across or to adjacent tissue structures by utilizing a thermally conductive, electrically non-conductive material.

SUMMARY

The present disclosure generally relates to an electrode sealing assembly for use with an electrosurgical instrument for sealing tissue. The electrode sealing assembly includes first and second jaw members which are movable from a first position in spaced relation relative to one another to at least one second position for grasping tissue therebetween. Each of the jaw members includes an insulative housing, a sealing plate and a thermally conductive, electrically non-conductive material disposed between the sealing plate and the insulative housing. Preferably, the insulative housing includes a series of electromechanical interfaces which mate with a corresponding series of electromechanical interfaces which depend from the sealing plate. The thermally conductive, electrically non-conductive material is configured to encapsulate and secure the sealing plate to the insulative housing. Alternatively, the thermally conductive, electrically non-conductive material may act as the insulative housing and the heat sink and, as such, would directly support the electrodes. Preferably, the electrically conductive sealing plate and the thermally conductive material include tissue contacting surfaces which are substantially flush relative to one another.

In one embodiment, the thermally conductive material includes first and second segments of anodized aluminum which join to encapsulate the sealing plate. Preferably, the thermally conductive material includes a series of fin-like extensions which laterally project therefrom. The fin-like extensions are designed to further absorb heat emanating from the sealing plates during activation. In another embodiment, the sealing plates include a series of stop members which project therefrom which are designed to control the distance between the jaw members when tissue is compressed therebetween. Preferably, the design of the thermally conductive material should maximize heat sink mass and surface contact with the air to maximize the heat sinking ability of the thermally conductive material. On the other hand, the design of the thermally conductive material should also minimize tissue contact to reduce/minimize overall mechanical damage to adjacent tissue structures.

Preferably, the insulating housing is made from a material selected from the group consisting of: nylon, syndiotactic-polystryrene, polybutylene terephthalate, polycarbonate, acrylonitrile butadiene styrene, polyphthalamide, polymide, polyethylene terephthalate, polyamide-imide, acrylic, polystyrene, polyether sulfone, aliphatic polyketone, acetal copolymer, polyurethane, nylon with polyphenylene-oxide dispersion and acrylonitrile styrene acrylate.

In another embodiment according to the present disclosure, the electrode sealing assembly includes an active cooling system disposed within at least one of the jaw members. Preferably, the active cooling system cools tissue adjacent the sealing plates to limit thermal spread during and after activation. Advantageously, a non-conductive fluid is used for the active cooling system.

In yet another embodiment according to the present disclosure, the electrode sealing assembly includes a thermally conductive, electrically non-conductive material disposed on a tissue engaging surface of at least one of the jaw members. Preferably, the thermally conductive, electrically non-conductive material includes a so called "cool polymer". It is envisioned that the cool polymer material will dissipate heat in a more isothermal profile to the surrounding environment resulting in a lower maximum temperature and reduced hot spots which may lead to undesirable thermal effects (thermal concentration in the electrode center). In still yet another embodiment according to the present disclosure, at least one of the jaw members includes a recessed portion which is designed to receive a portion of uncompressed tissue therein during activation of electrosurgical energy. It is contemplated that the moisture contained in the uncompressed tissue essentially acts as a heat sink to limit thermal spread to adjacent tissue.

Preferably, the electrode sealing assembly is removable, disposable and replaceable after the electrode sealing assembly is used beyond its intended number of activation cycles. Alternatively, the electrode sealing assembly may be integrally associated with the instrument and not removable. In this instance, the electrosurgical instrument (open or endoscopic) may be designed for single use applications and the entire instrument is fully disposable after the surgery is completed.

DETAILED DESCRIPTION

It has been found that by providing a thermally conductive and electrically non-conductive material adjacent to the electrically conductive sealing surfaces, surgeons can more readily and more easily produce a consistent, high quality seal and effectively reduce thermal spread across or to adjacent tissue. For the purposes herein the term "thermal spread" refers generally to the heat transfer (heat conduction, heat convection or electrical current dissipation) dissipating along the periphery of the electrically conductive or electrically active surfaces to adjacent tissue. This can also be termed "collateral damage" to adjacent tissue.

It is envisioned that the configuration of the thermally conductive material which surrounds the perimeter of the electrically conductive surface will effectively absorb heat during electrosurgical activation (or thermally dissipate the heat during electrosurgical activation) and generally restrict heat travel to areas between the opposing electrically conductive surfaces. In other words, the material acts like a so called "heat sink". As mentioned above, the thermally conductive material is also electrically non-conductive which also restricts current concentrations to between the two opposing surfaces.

It is important to note that this is different from dielectrically coating the outer surfaces of the instrument to prevent tissue "blanching" at points normal to the sealing site. These coatings are not designed or intended to reduce collateral tissue damage or thermal spread to adjacent tissue (tissue lying along the tissue sealing plane).

It is contemplated that by providing a thermally conductive material adjacent to the electrically conductive surface, the thermally conductive path is altered thereby influencing the thermal spread/collateral damage to adjacent tissue structures. In addition, the thermally conductive, electrically non-conductive material also isolates the two electrically opposing poles (i.e., electrodes) from one another thereby reducing the possibility that tissue or tissue fluids can create an unintended bridge or path for current travel to adjacent tissue. Preferably, the thermally conductive material and electrically conductive sealing surface are dimensioned such that the current is concentrated at the intended sealing site between the opposing electrically conductive surfaces as explained in more detail below.

Figure 1A:
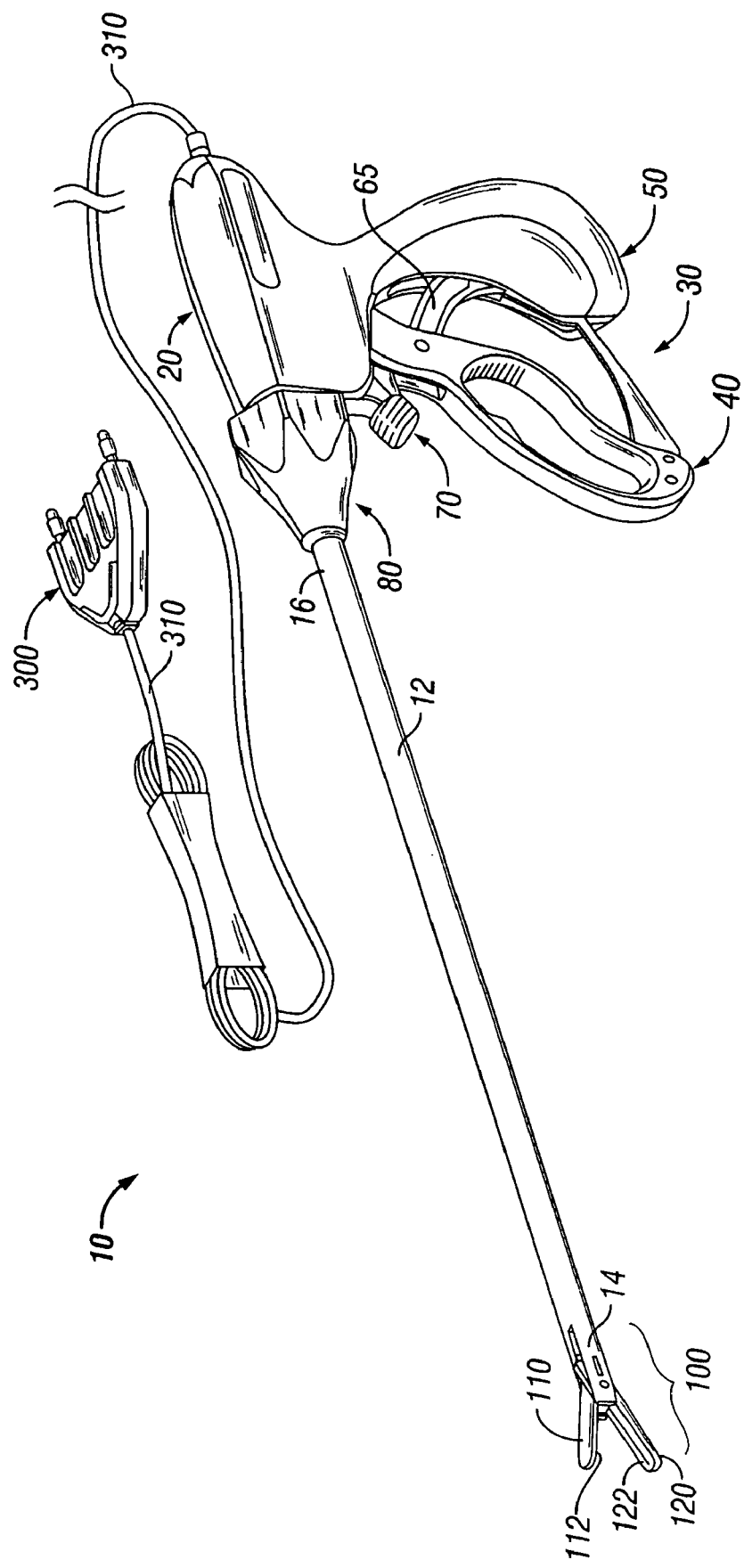
FIG. 1A is a perspective view of an endoscopic bipolar forceps which is configured to support an electrode sealing assembly according to the present disclosure.
Figure 1B:
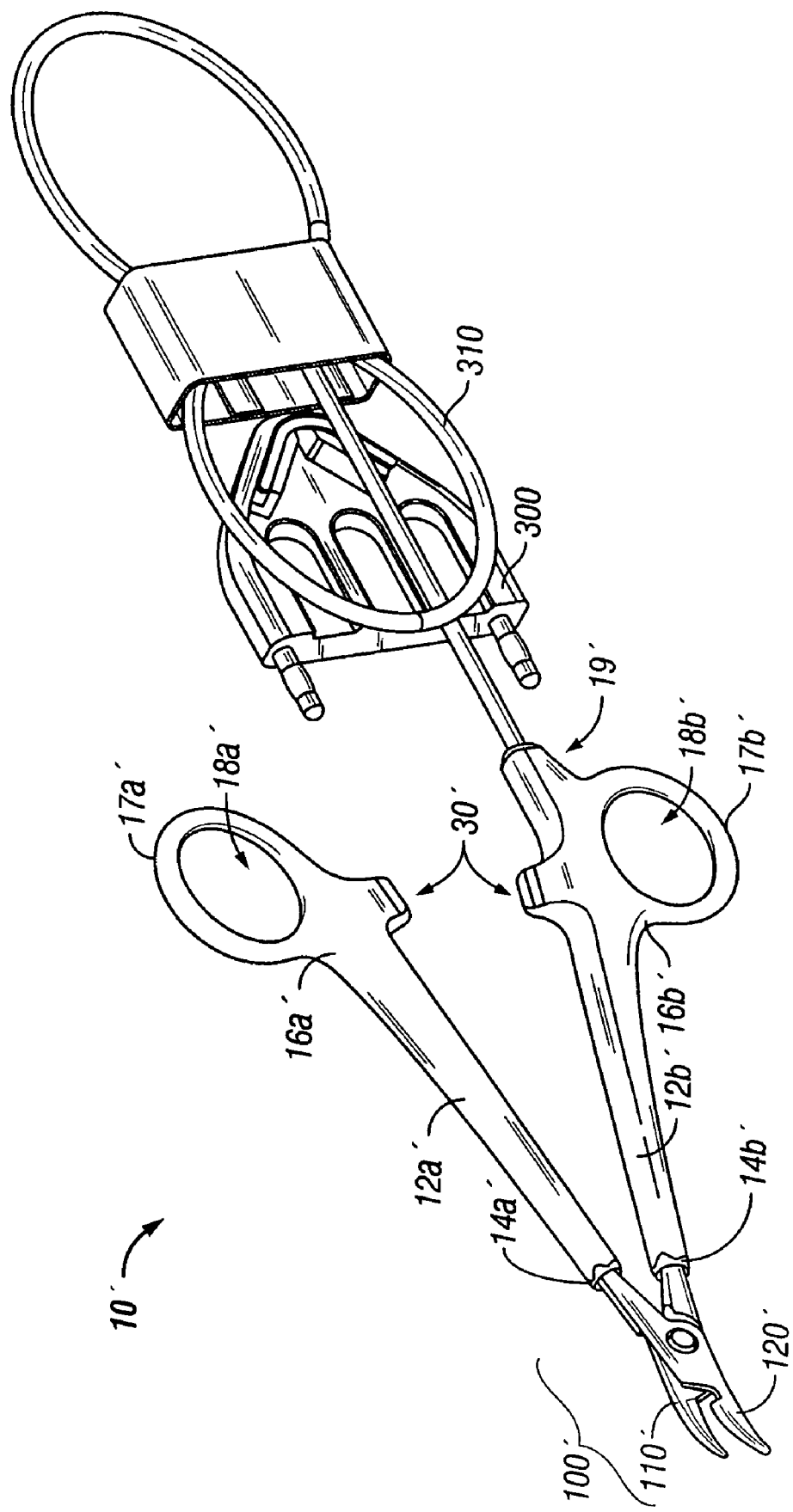
FIG. 1B is a perspective view of an open bipolar forceps which is configured to support the electrode sealing assembly according to the present disclosure.

Referring now to FIGS. 1A and 1B, two bipolar forceps 10 and 10' are shown; a first forceps 10 for use with endoscopic surgical procedures and a second forceps 10' for use with open surgical procedures. For the purposes herein, either an endoscopic instrument or an open instrument may be utilized for supporting the electrode sealing assembly according to the present disclosure. Obviously, different electrical and mechanical connections and considerations apply to each particular type of instrument, however, the novel aspects with respect to the electrode sealing assembly and its operating characteristics remain generally consistent with respect to both the open or endoscopic designs of FIGS. 1A and 1B. Forceps 10 and 10' are shown by way of example and other electrosurgical forceps are also envisioned which may support the electrode sealing assembly of the present disclosure. In the drawings and in the description which follows, the term "proximal", as is traditional, will refer to the end of the forceps 10, 10' which is closer to the user, while the term "distal" will refer to the end which is further from the user.

FIG. 1A shows one example of an endoscopic vessel sealing instrument 10 which is configured to support an electrode sealing assembly 100. More particularly, forceps 10 generally includes a housing 20, a handle assembly 30, a rotating assembly 80, a trigger assembly 70 and the end effector assembly 100 which mutually cooperate to grasp, seal and, if warranted, divide tissue. The forceps 10 includes a shaft 12 which has a distal end 14 dimensioned to mechanically engage the end effector assembly 100 and a proximal end 16 which mechanically engages the housing 20 proximate the rotating assembly 80.

Forceps 10 also includes a plug 300 which connects the forceps 10 to a source of electrosurgical energy, e.g., an electrosurgical generator (not shown) via an electrical cable 310. Handle assembly 30 includes a fixed handle 50 and a movable handle 40. Handle 40 moves relative to fixed handle 50 to actuate the end effector assembly 100 and enable a user to grasp and manipulate tissue 400 (See FIG. 6). More particularly, the end effector assembly 100 includes a pair of opposing jaw members 110 and 120 which move in response to movement of the handle 40 from an open position wherein the jaw members 110 and 120 are disposed in spaced relation relative to one another, to a clamping or closed position wherein the jaw members 110 and 120 cooperate to grasp tissue therebetween.

The housing 20 encloses a drive assembly (not shown) which cooperates with the movable handle 40 to impart movement of the jaw members 110 and 120 from the open position to the clamping or closed position. The handle assembly 30 can generally be characterized as a four-bar mechanical linkage which provides a unique mechanical advantage when sealing tissue between the jaw members 110 and 120. For example, once the desired position for the sealing site is determined and the jaw members 110 and 120 are properly positioned, handle 40 may be compressed fully to lock the jaw members 110 and 120 in a closed position against the tissue. The details relating to the inter-cooperative relationships of the inner-working components of forceps 10 are disclosed in commonly-owned U.S. patent application Ser. Nos. 10/284,562 and 10/460,926 which are both incorporated in their entirety by reference herein. When the jaw members 110 and 120 are fully compressed about the tissue, the forceps 10 is now ready for selective application of electrosurgical energy.

Experimental results suggest that the magnitude of pressure exerted on the tissue by the electrically conductive sealing surfaces 112, 122 of the jaw members 110 and 120, respectively, is important in assuring a proper surgical seal. Pressures within a working range of about 3 kg/cm$^2$ to about 16 kg/cm$^2$ and, preferably, within a working range of about 6 kg/cm$^2$ to about 13 kg/cm$^2$ have been shown to be effective for sealing various tissue types. Most preferably, the pressures are within a working range of about 4.5 kg/cm$^2$ to about 8.5 kg/cm$^2$ to optimize sealing.

An open forceps 10' for use in connection with traditional open surgical procedures and is shown by way of example in FIG. 1B. Open forceps 10' includes a pair of elongated shaft portions 12a', 12b' each having a proximal end 16a' and 16b', respectively, and a distal end 14a' and 14b', respectively. The forceps 10' includes jaw assembly 100' which attaches to the distal ends 14a' and 14b' of shafts 12a' and 12b', respectively. Jaw assembly 100' includes an upper jaw member 110' and a lower jaw member 120' which are movable relative to one another to grasp tissue therebetween.

Preferably, each shaft 12a' and 12b' includes a handle 17a' and 17b' disposed at the proximal end 16a' and 16b' thereof which each define a finger hole 18a' and 18b', respectively, therethrough for receiving a finger of the user. As can be appreciated, finger holes 18a' and 18b' facilitate movement of the shafts 12a' and 12b' relative to one another which, in turn, pivot the jaw members 110' and 120' from the open position wherein the jaw members 110' and 120' are disposed in spaced relation relative to one another for manipulating tissue to a clamping or closed position wherein the jaw members 110' and 120' cooperate to grasp tissue therebetween.

A ratchet 30' is included for selectively locking the jaw members 110' and 120' relative to one another at various positions during pivoting. Preferably, each position associated with the cooperating ratchet interfaces 30' holds a specific, i.e., constant, strain energy in the shaft members 12a' and 12b' which, in turn, transmits a specific closing force to the jaw members 110' and 120'. It is envisioned that the ratchet 30' may include graduations or other visual markings which enable the user to easily and quickly ascertain and control the amount of closure force desired between the jaw members 110' and 120'. One of the shafts, e.g., 12b', includes a proximal shaft connector/flange 19' which is designed to connect the forceps 10' to a source of RF energy (not shown) via an electrosurgical cable 310 and plug 300. The details relating to the inner-working electrical connections and various components of forceps 10' are disclosed in commonly-owned U.S. patent application Ser. No. 10/369,894 which is incorporated in its entirety by reference herein.

As mentioned above, two mechanical factors play an important role in determining the resulting thickness of the sealed tissue and effectiveness of the seal, i.e., the pressure applied between opposing jaw members 110' and 120' and the gap between the opposing jaw members 110' and 120' during the sealing process. Applying the correct force is also important for other reasons: to reduce the impedance of the tissue to a low enough value that allows enough current through the tissue; and to overcome the forces of expansion during the heating of the tissue in addition to contributing towards creating the required seal thickness necessary for a good seal.

For the purposes herein, electrode assemblies 100 and 100' include the same general configuration and are designed to reduce thermal spread to adjacent tissue. However, certain modifications may have to be made to each electrode sealing assembly 100 (or 100') to fit the electrode sealing assembly 100 (or 100') to a specific support structure for an open or endoscopic instrument. By controlling the intensity, frequency and duration of the RF energy applied to the tissue, the user can selectively seal the tissue as needed for a particular purpose. As can be appreciated, different tissue types and the physical characteristics associated with each tissue type may require different electrical sealing parameters.

Figure 2A:
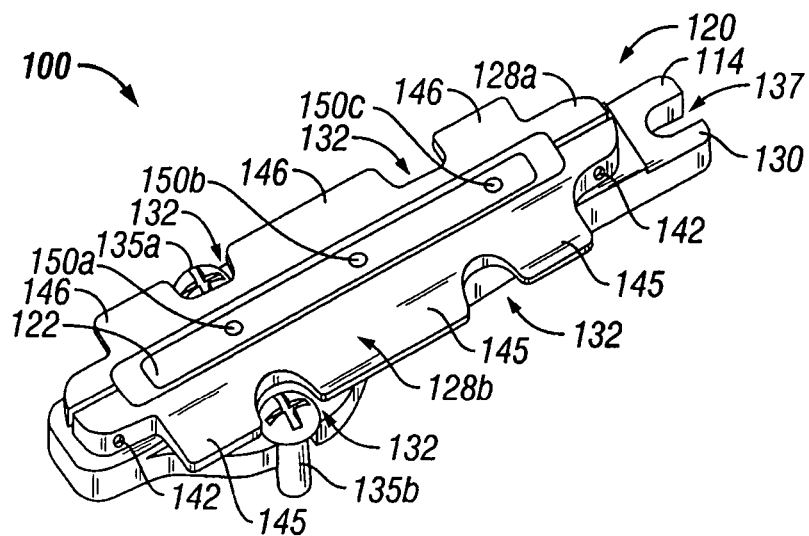
FIG. 2A is an enlarged, perspective view of the electrode sealing assembly according to the present invention.
Figure 2B:
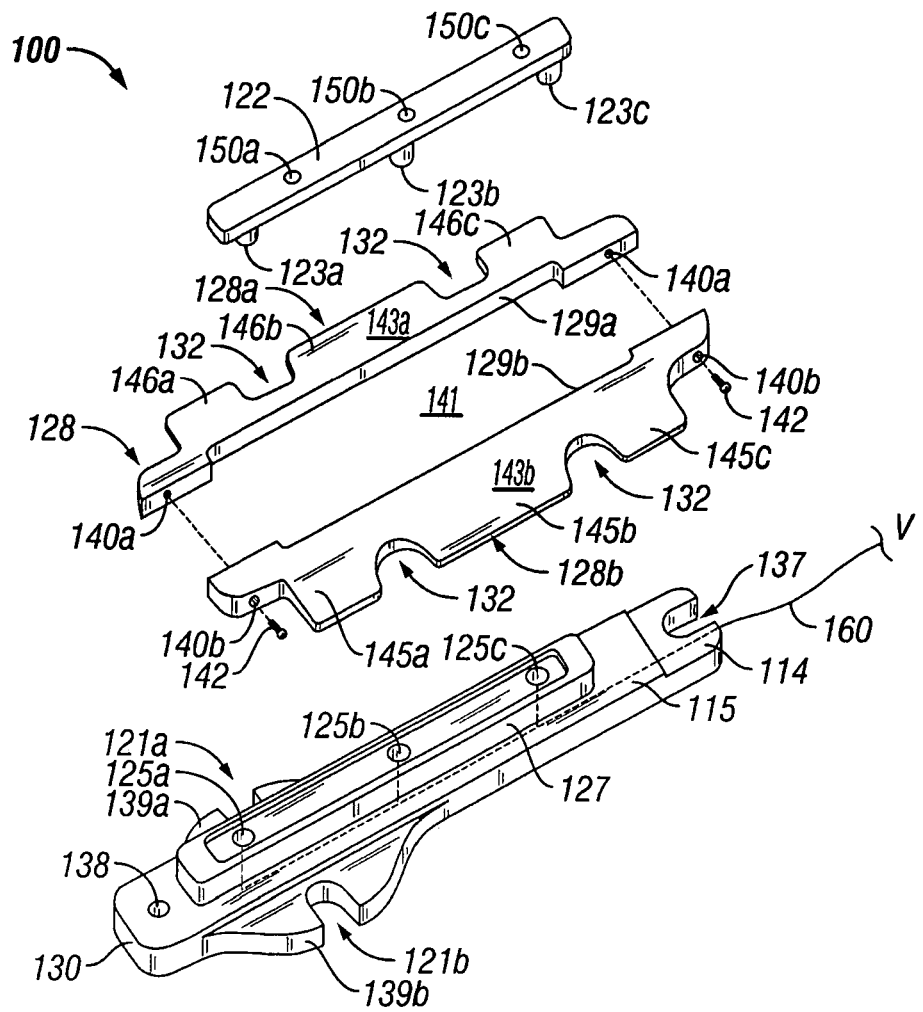
FIG. 2B is an enlarged, perspective view of the embodiment shown in FIG. 2A with parts separated.

FIGS. 2A and 2B show enlarged views of the lower jaw 120 of the electrode sealing assembly 100 (or 100') according to the present disclosure. As can be appreciated a second jaw 110 with similar components as described below is positioned in opposition to jaw member 120. Only the elements of jaw member 120 are described herein, however, jaw member 110 also includes identical or similar elements which are designed to accomplish similar purposes such that bipolar electrosurgical energy can be conducted through tissue held between the two jaw members 110 and 120 to effect a seal.

More particularly, lower jaw member 120 includes an insulated outer housing 114 which supports a thermally conductive, electrically non-conductive material 128 and electrically conductive sealing surface or sealing plate 122. As best seen in FIG. 2B, insulative housing 114 includes a support surface 115 which houses an electrode support step 127. Support step 127 includes a series of electro-mechanical interfaces 125a, 125b and 125c which matingly engage a set of corresponding interfaces 123a, 123b and 123c which depend from sealing plate 122. The outer periphery of the support step 127 is also preferably dimensioned to matingly engage the thermally conductive material 128 as will be explained in more detail below.

Each electromechanical interface, e.g., 125a, is electrically connected to an electrical potential by way of wire 160 which extends to the generator (not shown). It is envisioned that other electrical configurations are plausible as is known in the art and the above is shown by way of example. For example, electrically conductive tubes or plates may be utilized within the jaw members 110 and 120 to supply current to the sealing plate 122.

Support surface 115 also includes a series of notches 137, 121a, 121b and screw holes 138 which secure the insulative housing 114 to the electrode sealing assembly 100. For example, and as best shown in FIG. 2A, the support surface 115 includes a pair of flanges 139a and 139b which project laterally from the distal end of the support surface 115 and which are each dimensioned to receive the head of a screw 135a and 135b, respectively. In turn, the screws 135a and 135b secure the support surface to the electrode sealing assembly 100. A proximal notch 137 preferably mates with another screw (not shown) to position the end of the support surface 115 on the electrode sealing assembly 100. Other apertures, e.g., 138, may also be utilized to align and/or secure the support surface 115 on the electrode sealing assembly 100 during the manufacturing process.

Thermally conductive material 128 is preferably made from two laterally-opposing segments 128a and 128b which mate to encompass the sealing plate 122 and the support step 127 as best seen in FIG. 2A. A series of set screws or pegs 142 secure the two thermally conductive segments 128a and 128b about the sealing plate 122 and about the support step 127 once assembled. As mentioned above, the thermally conductive material 128 is designed to effectively absorb or thermally dissipate the heat during electrosurgical activation and generally restrict heat travel to areas between the opposing sealing plates 122. In other words, the material acts like a "heat sink" to limit thermal damage to surrounding tissue.

As mentioned above, the thermally conductive material 128 is also electrically non-conductive which also restricts current concentrations to between the two opposing sealing plates 122. Preferably, the thermally conductive material 128 is made from a material having a high thermal conductivity value or "k" value and minimum electrical conductively, e.g., anodized aluminum. Alternatively, the thermally conductive material 128 may be made from or combined with a semi-resilient or elastomeric material so as not to inflict mechanical damage to the tissue during compression. Mechanical damage may also be diminished by minimizing the overall tissue contact area of the thermally conductive material 128 (See, e.g., FIG. 3). Alternatively, a spring loaded system (not shown) designed to apply pressures below critical tissue pressure limits may be employed to reduce mechanical damage of the tissue when under compression.

Other compression-reducing systems are also envisioned to avoid over-compression of tissue adjacent the sealing plates 122 and between the opposing thermally conductive materials 128, e.g., rubber-like inserts, foam or the like. Other examples of thermally conductive and electrically non-conductive materials which can be utilized to minimize thermal damage to surrounding tissue include, but are not limited to: thermally conductive plastic materials which dissipate heat along a preferred isothermal profile to the surrounding environment resulting in a lower maximum temperature and reduced formation of hot spots. Examples of such materials are commonly sold under the trademark CoolPoly® by Cool Polymers, Inc., of Rhode Island and composite materials such as $ALO_2$.

As mentioned above, the thermally conductive material 128 includes two segments 128a and 128b which mate about the sealing plate 122 and the support step 127. More particularly, each segment 128a and 128b includes a tissue contacting surface 143a and 143b with a recessed portion 129a and 129b, respectively, along an inner peripheral edge of the tissue contacting surface 143a and 143b such that, once the two segments 128a and 128b are assembled they form a slot 141 for seating the sealing plate 122 therein. Preferably, the sealing plate 122 is seated to lie generally flush with or below the tissue contacting surfaces 143a, 143b of the thermally conductive segments 128a and 128b. It is also envisioned that the thickness (or height relative to the insulated housing 114) of the thermally conductive material 128 proximate the recessed portions 129a, 129b is about equal to the height of the step 127 plus the thickness of the sealing plate 122 such that, once assembled, the sealing plate 122 and the thermally conductive material 128 lie substantially flush or below within the sealing plane.

The thermally conductive segments 128a and 128b may also include a series of fin-like extensions 145a, 145b, 145c and 146a, 146b, 146c, respectively, which extend laterally therefrom. It is envisioned that the fin-like extensions 145a, 145b, 145c and 146a, 146b, 146c further absorb or dissipate heat emanating from the sealing plates 122 during or after activation. The fins 145a, 145b, 145c and 146a, 146b, 146c may also be shaped and dimensioned to facilitate manufacturing and assembly, i.e., the fins 145a, 145b, 145c and 146a, 146b, 146c may be shaped to include slots 132 therein which allow passage of one or more screws 135a, 135b which attach the insulative housing 114 to the underlying electrode sealing assembly 100.

As mentioned above, the sealing plate 122 is electromechanically connected to the underlying insulative housing 114 by virtue of a series of electromechanical interfaces 123a, 123b and 123c which project outwardly therefrom to mate with a series of corresponding electromechanical interfaces 125a, 125b and 125c. It is envisioned that the electromechanical interfacing elements 123a, 123b, 123c and 125a, 125b, 125c maintain electrical continuity from the insulative housing 114 to the sealing plate 122. As mentioned above, once assembled and interfaced with the insulative housing 114, the thermally conductive material 128 encapsulates and further secures the sealing plate 122 atop the insulative housing 114.

A series of stop members 150a, 150b and 150c is preferably disposed on the tissue contacting surfaces or the inner-facing surfaces of the electrically conductive sealing plates 122 (and/or the opposite sealing plate 112 (See FIG. 1A) on jaw member 110) to facilitate gripping and manipulation of tissue and to define a gap distance between opposing jaw members 110 and 120 (or 110' and 120') during sealing. In order to achieve a desired spacing between the electrically conductive plates 112, 122 of the respective jaw members 110, 120, (i.e., gap distance) and apply the required force to properly seal tissue, at least one jaw member 110 or 120 includes at least one stop member or stop members, e.g., 150a, 150b and 150c, which limit the movement of the two opposing jaw members 110 and 120 relative to one another. The stop members, e.g., 150a, extends from the sealing plate or tissue contacting surface 122 a predetermined distance according to the specific material properties of the stop member 150a(e.g., compressive strength, thermal expansion, etc.) to yield a consistent and accurate gap distance during sealing. The gap distance between opposing sealing surfaces 112, 122 (and the sealing surface (not shown) of jaw member 110) during sealing preferably ranges from about 0.001 inches to about 0.006 inches and, preferably, between about 0.002 inches and about 0.003 inches. For larger tissue structures such as bowel, lung or intestine the gap distance ranges from about 0.001 inches to about 0.012 inches and preferably from about 0.005 inches to about 0.007 inches.

Stop members 150a–150c are preferably made from an insulative material, e.g., parylene, nylon and/or ceramic. The stop members 150a–150c can be disposed on one or both of the jaw members 110 and 120 and may be dimensioned in a variety of different shapes and sizes, e.g., longitudinal, circular, ridge-like, etc.

The non-conductive stop members 150a–150c are molded onto the sealing plates 112 and 122 (e.g., overmolding, injection molding, etc.), stamped onto the sealing plates 112 and 122, deposited (e.g., plasma deposition) onto the sealing plates 112 and 122 and/or thermally sprayed onto the surface of the sealing plates 112 and 122 (e.g., a ceramic material may be thermally sprayed) to form the stop members 150a–150c. Many different configurations for the stop members 150a–150c are discussed in detail in commonly-assigned, co-pending U.S. application Ser. No. PCT/US01/11413 entitled "VESSEL SEALER AND DIVIDER WITH NON-CONDUCTIVE STOP MEMBERS" by Dycus et al. which is hereby incorporated by reference in its entirety herein.

It is also envisioned that the thermally conductive material 128 may be dimensioned thicker than the height of step 127 and the thickness of the sealing plate 122 such that the thermally conductive material 128 acts like a stop member for maintaining a gap distance between the sealing plates 122 during activation.

In addition to keeping the pressure within a working range (i.e., about 3 kg/cm$^2$ to about 16 kg/cm$^2$) and the gap distance within a specified range (i.e., about 0.001 inches to about 0.012 inches for large tissue structures) the electrical power should be kept within the range of about 1 W to about 350 W, about 1 Vrms to about 400 Vrms and about 0 Amps to about 5.5 Amps.

Preferably, thermal spread on each side of the sealing plates 122 is kept to less than about 2 mm and more preferably less than about 0.5 mm to promote tissue healing. However, when sealing larger or well-vascularized tissue structures, thermal spread is acceptable to about 5 mm. It is envisioned that maintaining the viability of tissue surrounding or adjacent the sealing site or fused tissue area will promote healing.

Figure 3:
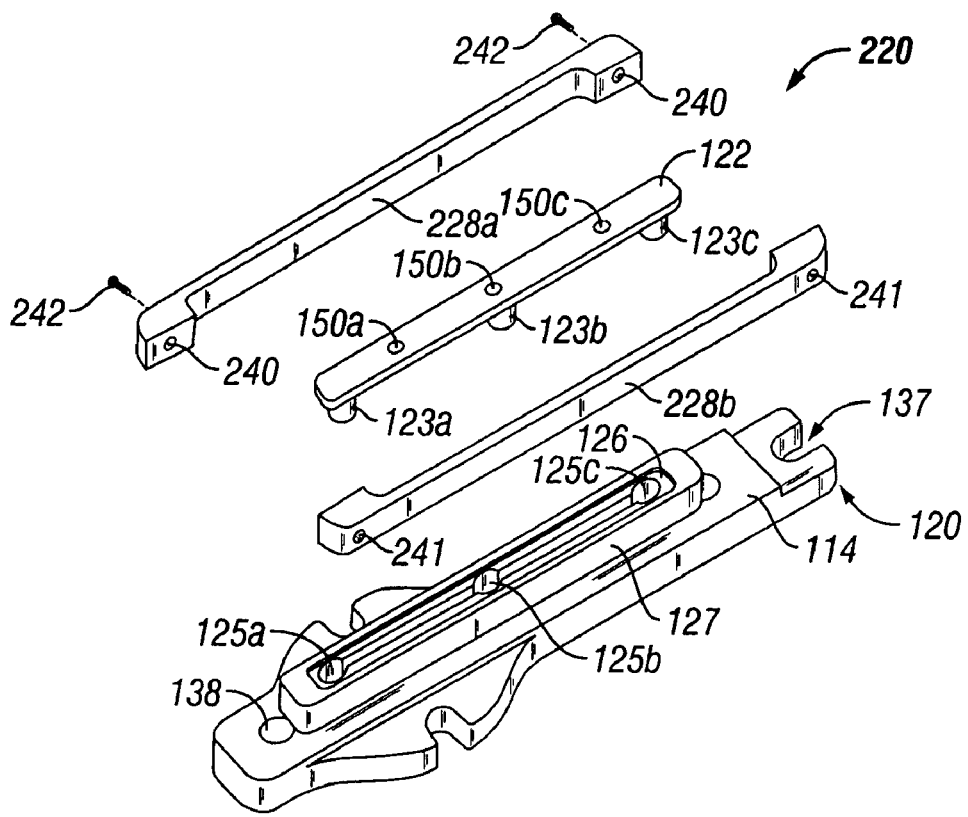
FIG. 3 is an enlarged, perspective view of an alternate, simplified embodiment of the electrode sealing assembly with parts separated according to the present disclosure.
Figure 4:
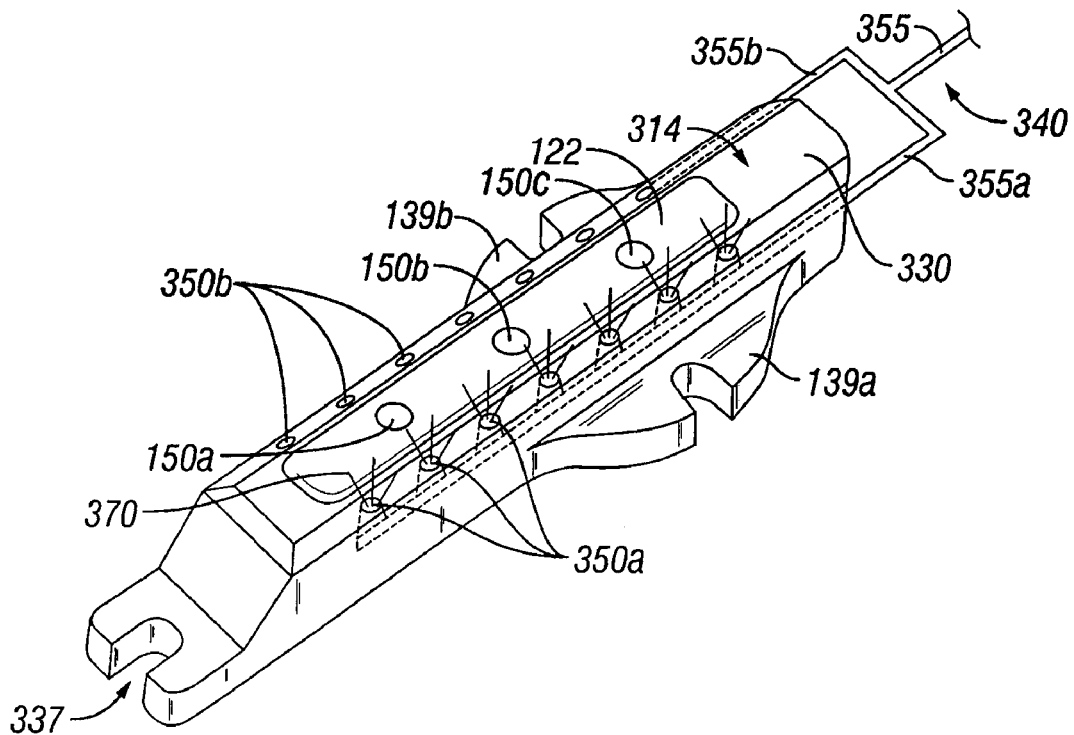
FIG. 4 is an enlarged, perspective view of an alternate embodiment of the electrode sealing assembly showing an active cooling system designed to reduce thermal spread during activation.

FIGS. 3 and 4 show alternate embodiments of lower jaw members 220 and 320 of the electrode sealing assembly 100 which may be utilized to reduce thermal spread to adjacent tissue during activation. More particularly, FIG. 3 shows a lower jaw member 220 which includes the same insulated housing 114 and sealing plate 122 configuration of FIGS. 2A and 2B. The thermally conductive material 228 is modified to have a reduced width which, as mentioned above, reduces the overall tissue contacting surface of the thermally conductive material 128. It is envisioned that mechanical damage may be diminished or at least maintained below critical tissue pressure limits by minimizing the overall tissue contact area of the thermally conductive material 128. Much in the same fashion as described above with respect to FIGS. 2A and 2B, the thermally conductive material 228 is secured about the sealing plate 122 and the step 127 by a series of screws 242 which mate into apertures 240 and 241 in segments 228a and 228b. As can be appreciated, the overall required width of the thermally conductive material 228 may be dependent upon type of tissue being sealed or the thickness of the tissue being sealed. Step 127 may include a reliefed portion 126 disposed therein which seats or aligns the sealing plate 122 during assembly.

FIG. 4 shows yet another possible configuration of the lower jaw member 320 of the electrode sealing assembly 100 (or 100') designed to reduce thermal spread to adjacent tissue. In this embodiment, a thermally conductive material is not utilized as the heat absorbing material or heat sink, but, rather, an active cooling system 340 surrounds the sealing plate 122 to reduce heat dissipation to surrounding tissue. More particularly, insulated housing 314 includes a series of ducts or tubes disposed therethrough which supply active cooling liquid (preferably, non-electrically conductive cooling liquid) or gas (e.g., air) 370 to a series of nozzles or ports 350a and 350b located on an upper surface 330 of the insulated housing 314. Preferably, the ports 350a and 350b are located immediately adjacent the sealing plate 122 and extend longitudinally on opposite sides thereof, i.e., ports 350a extend along one side of the sealing plate 122 and ports 350b extend along the opposite side of the sealing plate 122.

As can be appreciated, the sealing system 340 supplies coolant (liquid or gas (e.g., air)) 370 to the tissue areas adjacent the sealing plates 122 to actively cool the tissue during activation which reduces thermal spread. With respect to this particular embodiment and compared to the embodiments of FIGS. 2A–3, the insulated housing 314 encapsulates the sealing plate 122 by virtue of a mechanical connection or manufacturing process, e.g. stamp molding or injection molding.

Figure 5A:
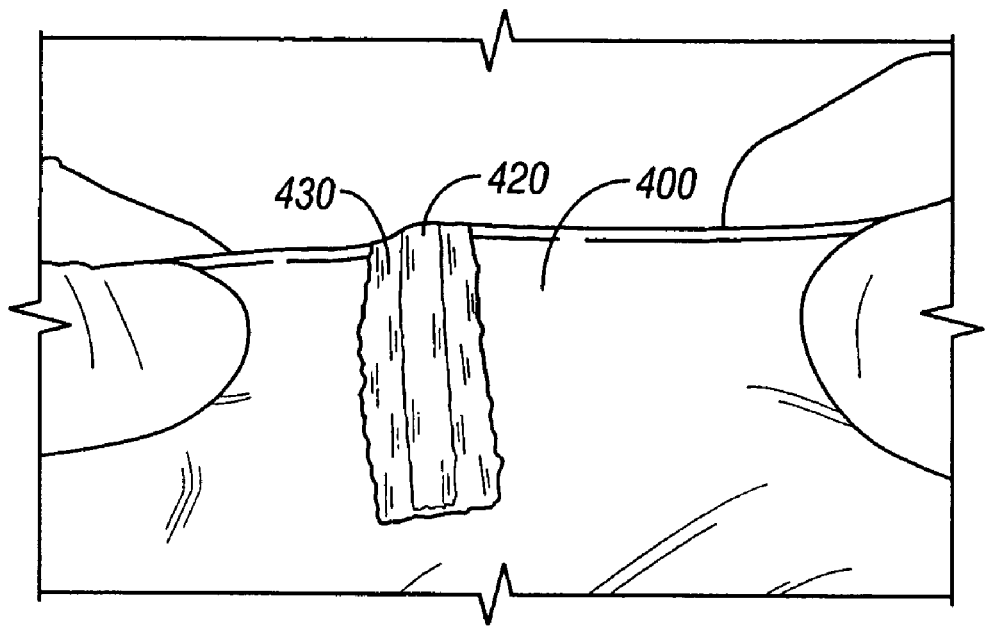
FIG. 5A is an enlarged view of a seal utilizing a conventional vessel sealing instrument with a conventional electrode sealing assembly.
Figure 5B:
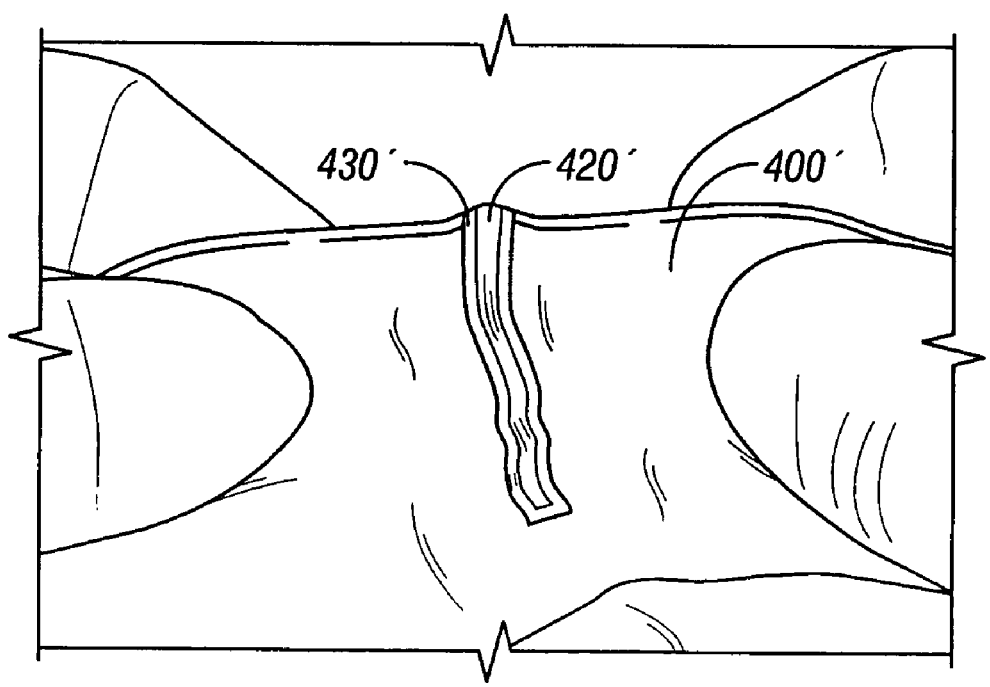
FIG. 5B is an enlarged view of a seal utilizing a vessel sealing instrument having the electrode sealing assembly according the present disclosure.

FIGS. 5A and 5B show a side-by-side comparison of the resulting tissue seals 420 and 420' utilizing a prior vessel sealing instrument (See FIG. 5A) and a vessel sealing instrument designed to reduce thermal spread to adjacent tissue 400 according to the present disclosure (See FIG. 5B). More particularly and with respect to FIG. 5A, there is some notable thermal damage 430 to adjacent tissue 400 proximate the tissue seal 420. FIG. 5B shows the resulting seal 420' utilizing one of the various electrode assemblies 100 (or 100') described herein. A more uniform and narrower seal 420' is evident with a significant reduction of thermal damage 430' to adjacent tissue 400. It is envisioned that reducing thermal damage to adjacent tissue 400 can improve healing especially in sensitive tissue areas, e.g., small and large intestines. As mentioned above, the thermal spread is preferably kept to about 2 mm with sensitive large tissues and vessels and about 5 mm with non-sensitive tissues and vessels.

Figure 6:
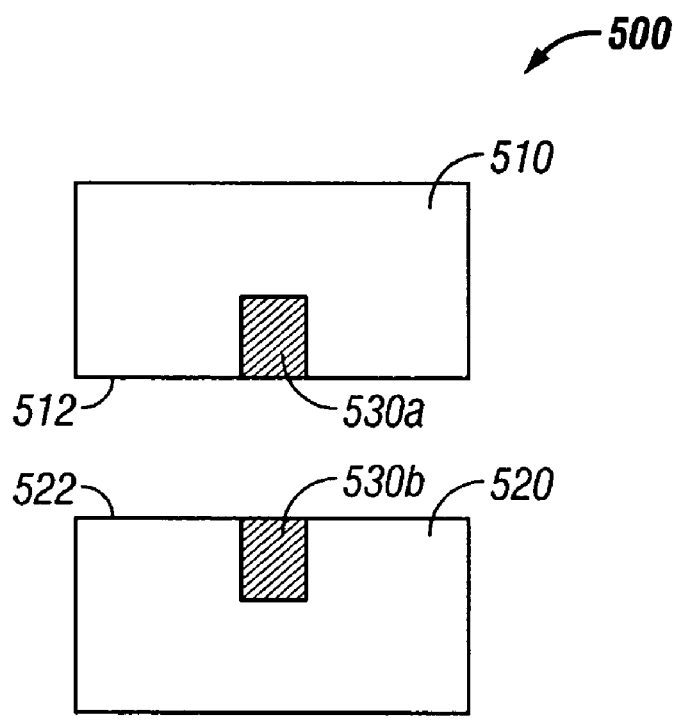
FIG. 6 is a schematic, end view of an alternate electrode sealing assembly which may be utilized to reduce thermal spread during activation.

FIG. 6 shows an alternative electrode sealing assembly 500 which is also designed to reduce thermal spread to adjacent tissue. More particularly, electrode sealing assembly 500 includes upper and lower jaws 510 and 520, respectively, which each include a thermally conductive, electrically insulative material 530a and 530b, e.g., a so-called "cool polymer" material, disposed on (or within) the respective tissue sealing plates, 512 and 522. Preferably, the cool polymers 530a, 530b are centrally disposed within each sealing plate 512 and 522, respectively. It is envisioned that the cool polymers 530a and 530b will act as heat sinks (i.e., absorb heat) during activation which will limit the thermal spread to adjacent tissue 400. Examples of cool polymers include thermally conductive plastic materials which dissipate heat in a more isothermal profile to the surrounding environment resulting in a lower maximum temperature and reduced formation of hot spots such as materials commonly sold under the trademark CoolPoly® by Cool Polymers, Inc., of Rhode Island.

Figure 7:
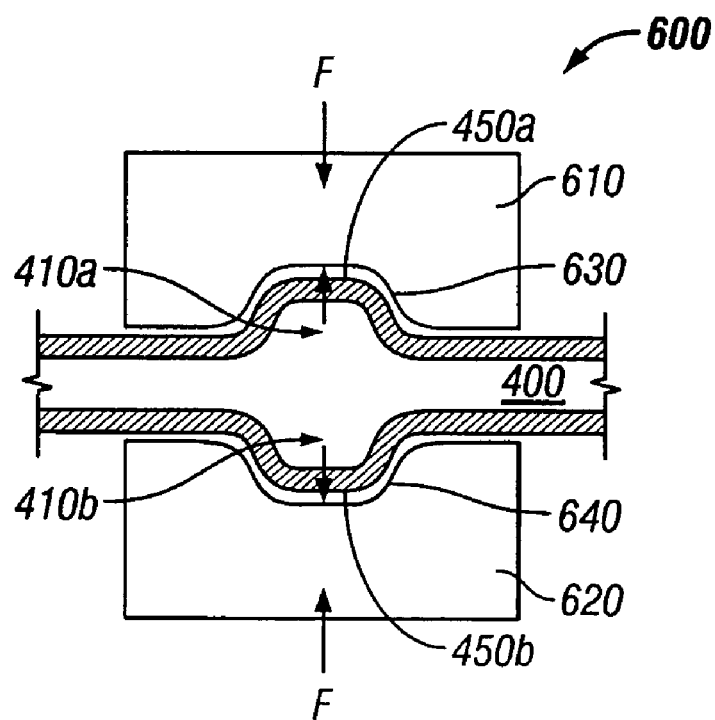
FIG. 7 is a schematic, end view of another alternate electrode sealing assembly which may be utilized to reduce thermal spread during activation.

FIG. 7 shows yet another electrode sealing assembly 600 which is also designed to reduce thermal spread to adjacent tissue 400. More particularly, electrode sealing assembly 600 includes upper and lower jaw members 610 and 620, respectively which are designed to engage tissue 400 therebetween. Each of the jaw members 610 and 620 includes a recessed portion 630 and 640, respectively which is dimensioned to allow bulging portions 450a and 450b of the tissue 400 to bulge into each respective jaw member 610 and 620 when the tissue 400 is under compression. It is envisioned that the moisture in the less-compressed tissue bulges 450a and 450b essentially acts as a heat sink to absorb heat during activation and reduce thermal spread to surrounding tissue.

It is envisioned that the jaw members 110 and 120 may be curved in order to reach specific anatomical structures and promote more consistent seals for certain procedures. For example, it is contemplated that dimensioning the jaw members 110 and 120 at an angle of about 45 degrees to about 70 degrees is preferred for accessing and sealing specific anatomical structures relevant to prostatectomies and cystectomies, e.g., the dorsal vein complex and the lateral pedicles. Other angles may be preferred for different surgical procedures.

Figure 8A:
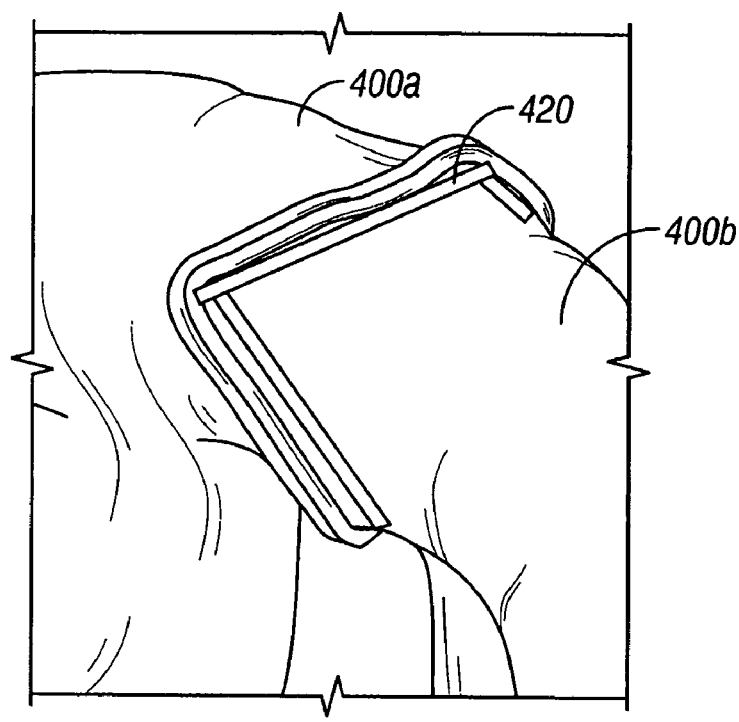
FIG. 8A shows a perspective view of a sealed tissue area of an end-to-end anastomosis utilizing a straight electrode sealing assembly according to the present disclosure.
Figure 8B:
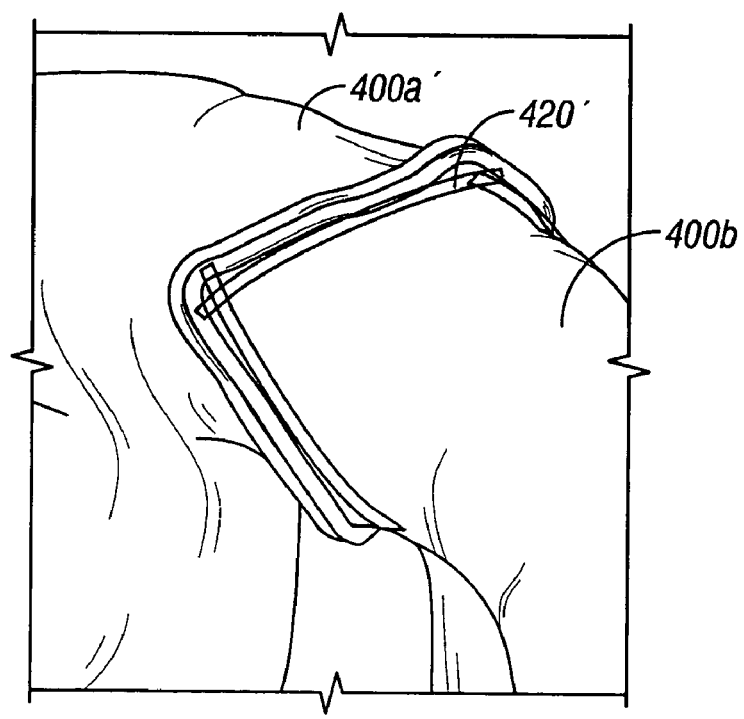
FIG. 8B shows a perspective view of a sealed tissue area of an end-to-end anastomosis utilizing a curved electrode sealing assembly according to the present disclosure.

For example and as best shown in FIGS. 8A and 8B, it may be preferable to use a curved jaw member (not shown) for an end-to-end anastomosis of bowel tissues. FIG. 8A shows the resulting seal 420 of an end-to-end anastomosis of two bowel segments 400a and 400b utilizing a straight pair of jaw members. FIG. 8B shows a resulting seal 420' of an end-to-end anastomosis of two bowel segments 400a' and 400b' utilizing a curved pair of jaw members. As can be appreciated the resulting seal 420' from the curved pair of jaw members tends to more closely conform to the general contours of the two tissue segments 400a' and 400b' which is envisioned will promote tissue healing around the anastomosis site.

It is also envisioned that the jaw members 110 and 120 may be tapered which is advantageous for two reasons: 1) the taper will apply constant pressure for a constant tissue thickness at parallel; 2) the thicker proximal portion of each jaw member 110 and 120 will resist bending due to the reaction force of the tissue 400.

From the foregoing and with reference to the various figure drawings, those skilled in the art will appreciate that certain modifications can also be made to the present disclosure without departing from the scope of the same. For example, although it is preferable that jaw members 110 and 120 meet in parallel opposition, and, therefore, meet on the same plane, in some cases it may be preferable to slightly bias the jaw members 110 and 120 to meet each other at the distal end such that additional closure force on the handles is required to deflect the electrodes in the same plane. It is envisioned that this could improve seal quality and/or consistency. Alternatively, the jaws members 110 and 120 may be configured to close in a heel-based manner or in an independently floating (with respect to parallel) fashion.

It is also envisioned that the above forceps 10 (or 10') may be utilized in connection with a closed-loop RF control system which optimizes sealing based upon pre-surgical conditions or changes in physical or electrical conditions during sealing. One example of a closed-loop control system is described in commonly-owned and concurrently-filed U.S. patent application Ser. No. 10/427,832 entitled "METHOD AND SYSTEM FOR CONTROLLING OUTPUT OF RF MEDICAL GENERATOR" and commonly-owned and concurrently-filed U.S. patent application Ser. No. [U.S. Provisional No. 60/466,954] entitled "METHOD AND SYSTEM FOR PROGRAMMING AND CONTROLLING AN ELECTROSURGICAL GENERATOR SYSTEM" which are both incorporated in their entirety by reference herein. In general, the closed-loop control, system includes a user interface for allowing a user to select at least one pre-surgical parameter, such as the type of surgical instrument operatively connected to the generator, the type of tissue and/or a desired surgical effect. A sensor module is also included for continually sensing at least one of electrical and physical properties proximate the surgical site and generating at least one signal relating thereto.

The closed loop control system also includes a control module for continually receiving or monitoring surgical parameters and each of the signals from the sensor module and processing each of the signals in accordance with a desired surgical effect using a microprocessor, computer algorithm and/or a look-up table. The control module generates at least one corresponding control signal relating to each signal from the sensor module(s), and relays the control signal to the electrosurgical generator for controlling the generator. The closed loop system may be employed in a feedback circuit or part of a surgical method for optimizing a surgical seal. The method includes the steps of: applying a series of electrical pulses to the surgical site; continually sensing electrical and physical properties proximate the surgical site; and varying pulse parameters of the individual pulses of the series of pulses in accordance with the continually-sensed properties. Alternatively, the signal may be continuous.

It is also contemplated that the sealing surfaces 122 of the jaw members 110 and 120 can be made from or coated with non-stick materials to reduce tissue adhesion. Alternatively, the jaw members 110 and 120 may be surface treated, roughened, to reduce sticking, e.g., bead blasting, stamping. When utilized on the sealing surfaces 122, these materials provide an optimal surface energy for eliminating sticking due in part to surface texture and susceptibility to surface breakdown due to electrical effects and corrosion in the presence of biologic tissues. It is envisioned that these materials exhibit superior non-stick qualities over stainless steel and should be utilized on the forceps 10 (or 10') in areas where the exposure to pressure and RF energy can create localized "hot spots" more susceptible to tissue adhesion. As can be appreciated, reducing the amount that the tissue "sticks" during sealing improves the overall efficacy of the instrument.

The non-stick materials may be manufactured from one (or a combination of one or more) of the following "non-stick" materials: nickel-chrome, chromium nitride, MedCoat 2000, Inconel 600 and tin-nickel. For example, high nickel chrome alloys, Ni200, Ni201(~100% Ni) may be made into electrodes or sealing surfaces by metal injection molding, stamping, machining or any like process. Also and as mentioned above, the sealing surfaces 122 may also be "coated" with one or more of the above materials to achieve the same result, i.e., a "non-stick surface".

One particular class of materials disclosed herein has demonstrated superior non-stick properties and, in some instances, superior seal quality. For example, nitride coatings which include, but not are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reduce overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 122 made from or coated with Ni200, Ni201(~100% Ni) also showed improved non-stick performance over typical bipolar stainless steel electrodes. It is also envisioned that the outer surface of the jaw members 110 and 120 may include a nickel-based material or coating which is designed to reduce adhesion between the jaw members 110, 120 with the surrounding tissue during or after sealing.

It is further envisioned that thermal spread may be reduced by altering the physical dimensions of the insulative housing 114. For example, in some cases it may be preferable to manufacture the insulative housing 114 from a variety of materials (either alone or in combination) which include: nylons and syndiotactic polystryrenes such as QUESTRA® manufactured by DOW Chemical; Polybutylene Terephthalate (PBT); Polycarbonate (PC); Acrylonitrile Butadiene Styrene (ABS); Polyphthalamide (PPA); Polymide, Polyethylene Terephthalate (PET); Polyamide-imide (PAI); Acrylic (PMMA); Polystyrene (PS and HIPS); Polyether Sulfone (PES); Aliphatic Polyketone; Acetal (POM) Copolymer; Polyurethane (PU and TPU); Nylon with Polyphenylene-oxide dispersion; and Acrylonitrile Styrene Acrylate.

It is also contemplated that only one of the two jaw members 110 and 120 may include one of the aforedescribed mechanisms or configurations for reducing thermal spread. For example and with reference to FIGS. 2A, 2B and 3, it is contemplated that only the lower jaw member 120, 220 may include the thermally conductive material 128, 228 disposed between the insulative housing 114 and the sealing plate 122. With reference to FIG. 4, only the lower jaw member 320 may include the active cooling system 340. With reference to FIG. 6, only the top jaw member 510 may be configured to house a cool polymer 530a for reducing thermal spread to adjacent tissue 400. Likewise and with reference to FIG. 7, only the upper jaw member 610 may include a recessed area 630 for receiving bulging tissue 450a. It is further contemplated that the above configurations may be used in combination to reduce thermal spread to adjacent tissue. For example, a cool polymer 530a may be used in combination with the thermally conductive material 128 of FIG. 2A or used in replace of the thermally conductive material 128 of FIG. 2A depending upon a particular purpose.

It is envisioned that the forceps 10 or 10' may be designed such that it is fully or partially disposable depending upon a particular purpose or to achieve a particular result. For example, electrode sealing assembly 100 may be selectively and releasably engageable with the distal end 14 of the shaft 12 and/or the proximal end 16 of shaft 12 may be selectively and releasably engageable with the housing 20 and the handle assembly 30. In either of these two instances, the forceps 10 would be considered "partially disposable" or "reposable", i.e., a new or different electrode sealing assembly 100 (or electrode sealing assembly 100 and shaft 12) selectively replaces the old jaw assembly 110 as needed.

While various embodiments of the disclosure have been described, it is not intended that the disclosure be limited thereto, as it is intended that the disclosure be as broad in scope as the art will allow and that the specification be read likewise. Therefore, the above descriptions should not be construed as limiting, but merely as exemplifications of preferred embodiments. Those skilled in the art will envision other modifications within the scope and spirit of the claims appended hereto.

What is claimed is:

1. An electrode sealing assembly designed for use with an electrosurgical instrument for sealing tissue, comprising:
   first and second jaw members each having an insulative housing including at least one electromechanical interface and being movable from a first position in spaced relation relative to one another to at least one second position for grasping tissue therebetween, each of the jaw members including:

an electrically conductive sealing plate having at least one corresponding electromechanical interface which mates with the electromechanical interface of the insulative housing;

a thermally conductive, electrically non-conductive material disposed between the insulative housing and the electrically conductive sealing plate, the thermally conductive, electrically non-conductive material configured to engage at least one side of said sealing plate; and wherein the thermally conductive, electrically non-conductive material of at least one of the first and second jaw members includes projections which extend laterally from an outer periphery of the insulative housing.

2. An electrode sealing assembly according to claim 1 wherein said thermally conductive, electrically non-conductive material is configured to encapsulate and secure the sealing plate to the insulative housing.

3. An electrode sealing assembly according to claim 1 wherein the thermally conductive, electrically non-conductive material of at least one of the first and second jaw members includes first and second segments which join to encapsulate the sealing plate.

4. An electrode sealing assembly according to claim 1 wherein the insulative housing of at least one of the first and second jaw members is made from a material selected from the group consisting of: nylon, syndiotactic-polystryrene, polybutylene terephthalate, polycarbonate, acrylonitrile butadiene styrene, polyphthalamide, polymide, polyethylene terephthalate, polyamide-imide, acrylic, polystyrene, polyether sulfone, aliphatic polyketone, acetal copolymer, polyurethane, nylon with polyphenylene-oxide dispersion and acrylonitrile styrene acrylate.

5. An electrode sealing assembly according to claim 1 wherein the thermally conductive, electrically non-conductive material of at least one of the first and second jaw members is at least one of thermally conductive plastic and anodized aluminum.

6. An electrode sealing assembly according to claim 1 wherein the electrically conductive sealing surface of at least one of the first and second jaw members includes at least one stop member for controlling the distance between jaw members.

7. An electrode sealing assembly according to claim 1 wherein the electrically conductive sealing plate and the thermally conductive, electrically non-conductive material of at least one of the first and second jaw members include tissue contacting surfaces which are substantially flush relative to one another.

8. An electrode sealing assembly according to claim 1 wherein the jaw members are disposed at an angle relative to a shaft of the electrosurgical instrument.

9. An electrode sealing assembly according to claim 1 wherein the electrode sealing assembly is disposable.

10. An electrode sealing assembly according to claim 1 wherein the insulative housing of at least one of the first and second jaw members includes a support step which extends relative to an upper surface of the insulative housing, the support step being dimensioned to support the sealing plate thereon.

11. An electrode sealing assembly designed for use with an electrosurgical instrument for sealing tissue, comprising:
first and second jaw members being movable from a first position in spaced relation relative to one another to at least one second position for grasping tissue therebetween, each of the jaw members including:

an insulative housing having at least one electromechanical interface, the insulative housing of at least one of the first and second jaw members including a support step which extends relative to an upper surface of the insulative housing;

an electrically conductive sealing plate having at least one corresponding electromechanical interface which mates with the electromechanical interface of the insulative housing, at least one of the sealing plates of at least one of the of the first and second jaw members including at least one stop member which extends therefrom; and first and second thermally conductive, electrically non-conductive segments disposed between the insulative housing and the electrically conductive sealing plate, the thermally conductive, electrically non-conductive segments being joinable to encapsulate the support step to secure the sealing plate to the insulative housing.

12. An electrode sealing assembly designed for use with an electrosurgical instrument for sealing tissue, comprising:
first and second jaw members being movable from a first position in spaced relation relative to one another to at least one second position for grasping tissue therebetween, each of the jaw members including:

an insulative housing; and an electrically conductive sealing plate; and a thermally conductive, electrically non-conductive material being configured to engage a side of the sealing plate; and wherein the thermally conductive, electrically non-conductive material of at least one of the first and second jaw members includes projections which extend laterally from an outer periphery of the insulative housing.

13. An electrode sealing assembly according to claim 12 wherein said thermally conductive, electrically non-conductive material is configured to encapsulate and secure the sealing plate to the insulative housing.

14. An electrode sealing assembly designed for use with an electrosurgical instrument for sealing tissue, comprising:
first and second jaw members each having an insulative housing including at least one electromechanical interface and being movable from a first position in spaced relation relative to one another to at least one second position for grasping tissue therebetween, each of the jaw members including:

an electrically conductive sealing plate having at least one corresponding electromechanical interface which mates with the electromechanical interface of the insulative housing;

a thermally conductive, electrically non-conductive material disposed between the insulative housing and the electrically conductive sealing plate, the thermally conductive, electrically non-conductive material configured to engage at least one side of said sealing plate; and wherein the insulative housing of at least one of the first and second jaw members includes a support step which extends relative to an upper surface of the insulative housing, the support step being dimensioned to support the sealing plate thereon.

* * * * *